(12) United States Patent
Han et al.

(10) Patent No.: US 8,069,733 B2
(45) Date of Patent: Dec. 6, 2011

(54) DEVICE AND METHOD FOR MEASURING ELECTROMECHANICAL PROPERTIES AND MICROSTRUCTURE OF NANO-MATERIALS UNDER STRESS STATE

(75) Inventors: Xiaodong Han, Beijing (CN); Pan Liu, Beijing (CN); Yuefei Zhang, Beijing (CN); Yonghai Yue, Beijing (CN); Ze Zhang, Beijing (CN)

(73) Assignee: Beijing University of Technology, Beijing (CN)

( * ) Notice: Subject to any disclaimer, the term of this patent is extended or adjusted under 35 U.S.C. 154(b) by 246 days.

(21) Appl. No.: 12/632,597

(22) Filed: Dec. 7, 2009

(65) Prior Publication Data

US 2010/0154557 A1 Jun. 24, 2010

(30) Foreign Application Priority Data

Dec. 19, 2008 (CN) .......................... 2008 1 0240516

(51) Int. Cl.
*G01L 1/04* (2006.01)
(52) U.S. Cl. .......................................... 73/781; 73/782

(58) Field of Classification Search ................ 73/781, 73/782
See application file for complete search history.

(56) References Cited

U.S. PATENT DOCUMENTS

| | | | | |
|---|---|---|---|---|
| 4,912,822 A * | 4/1990 | Zdeblick et al. | ............. | 29/25.35 |
| 5,276,672 A * | 1/1994 | Miyazaki et al. | ................ | 73/105 |
| 5,606,162 A * | 2/1997 | Buser et al. | ...................... | 73/105 |
| 7,827,660 B2 * | 11/2010 | Gogoi et al. | ................. | 29/25.35 |
| 2006/0018239 A1 * | 1/2006 | Nam et al. | .................... | 369/126 |
| 2011/0107472 A1 * | 5/2011 | Han et al. | ......................... | 850/53 |

* cited by examiner

*Primary Examiner* — Lisa Caputo
*Assistant Examiner* — Punam Roy
(74) *Attorney, Agent, or Firm* — J.C. Patents

(57) ABSTRACT

A device for measuring electromechanical properties and microstructure of nano-materials under stress state comprises two bimetallic strips placed on an insulated metal ring plated with insulating paint, wherein the two bimetallic strips are placed in parallel or V-shaped to insulated metal ring on the same plane, one end of each bimetallic strip is fixed on the insulated metal ring, the other end of the bimetallic strip hangs inside of the insulated ring, the distance of two bimetallic strips were controlled within 0.002-1 mm. Also provided is a method for measuring electromechanical properties and microstructure of nano-materials under stress state.

3 Claims, 5 Drawing Sheets

DEVICE AND METHOD FOR MEASURING ELECTROMECHANICAL PROPERTIES AND MICROSTRUCTURE OF NANO-MATERIALS UNDER STRESS STATE

CROSS-REFERENCE TO RELATED APPLICATION

This application claims priority benefit of Chinese application No. 200810240516.8 filed on Dec. 19, 2008, the contents of which are hereby incorporated by reference in its entirety.

TECHNICAL FIELD OF THE INVENTION

The present invention relates to an apparatus and method for measuring electro-mechanical properties of nano-materials by in situ high resolution transmission electron microscope (TEM). More specifically, the present invention pertains to a TEM sample support or grid that allows the dynamic and real-time measure of the mechanical- electrical-microstructural relationships of individual nanostructure under stress field by in situ TEM at atomic lattice resolution level.

BACKGROUND OF THE INVENTION

As the basic building blocks of the nano-devices, nano-scale materials carry the information transport, storage and other important functions.

The interest in the trend to reduce the dimensions of these devices in the semiconductor and information industries has given rise to a necessity for developing techniques for studying microstructure and the size effects on the mechanical strength and charge transport properties of individual functional nanostructure under external stress field and electric field.

Transmission electron microscopy (TEM) is a powerful tool for characterizing the micro-structures of solid state materials in the field of nano-science and nanotechnology. TEM grid is used to support the detected samples, which is usually Cu grid 3 mm in diameter with thin carbon film coatings. But at present the TEM grid is effective only for the static testing, and not for in situ manipulation and dynamic testing at the nanoscale even to atomic scale level.

In situ TEM experiments provide direct visualization and description of the events as they happen and give qualitative information about the structure-property-processing relationships. These knowledge are vital to not only the design and functional the nanodevices and but also the reliability and service.

Several approaches have been studies for in situ electron microscopy manipulating, measuring and imaging the structure-property relationships of individual nanotub or nanowire.

One technique is described in "Physics review letters, vol. 94, 236802,2005" by Z. F. Ren. They combined the scanning tunnel microscopy probe with transmission electron microscopy, which revealed that the intrinsic properties of super plastic deformation of carbon nanotubes under electrifying state.

Another method for in situ electron microscopy testing one-dimentional nanostructure is reported in "Proceedings of the National Academy of Sciences, Vol. 102, No. 41, p. 14503-14508, 2005." by H. D. Espinosa. They developed a microelectromechanical systems (MEMS) based testing unit for in situ TEM mechanical testing of nanotubes, nanowires and thin films.

The above mentioned methods integrated the scanning tunneling microscopy probe or MEMS unit with the TEM holder, thereby enabling simultaneous TEM and mechanical measurements, for investigating the relationship between microstructure and interaction of individual nanostructure. But installing these devices inside the TEM holder that causes the holder can tilt a small angle or only a single axis tilting because of the narrow pole-piece gap. However, atomic scale lattice resolution of a crystal is only achieved when a low-indexed zone axis of a crystal is precisely aligned parallel to the electron beam. This condition is difficult to fulfill in these in situ measuring systems that are subjected to mechanical manipulation influence during the experiments.

SUMMARY OF THE INVENTION

The present invention provides an apparatus and a method that overcomes the aforementioned limitations and fills the aforementioned needs by provide a method and TEM sample holder or support for measuring the electro-mechanical-property relationships of individual nanostructure by in situ high resolution TEM dynamic observation.

1. Accordingly, the present invention has unique structural design of the TEM sample grid that is movably with two thermal bimetallic strips which realize the plane tensile or compressive deformation of individual nano-materials in situ TEM. It is an object of the invention to provide a sample grid for high resolution electron microscopy which can be installed in the commercial TEM specimen heating holder. The grid has a simple structure with the characteristics of reliable performance and inexpensive manufacture. The grid with two movable thermal bimetallic strips can fulfill the dynamic observation by heating the thermal bimetallic strips. The grid can fulfill the large tilt angle of X /Y-axial when in situ experiments which realize the dynamic sequential atomic resolution images.

2. It is a further object the invention to provide the fabrication method of individual nano-materials for in situ electron microscopy investigation such as one-dimensional nanowires, two-dimensional nano-films etc. The nano-materials are fabricated by lithography processes which is convenient for the nano-materials to be transferred and positioned on two bimetallic strips for in situ TEM investigation and measurement of the mechanical-electrical-microstructure of the nano-materials in the atomic lattice resolution.

3. It is yet another object of the invention to provide a measurement method of the correlation of mechanical-electrical-microstructure at atomic level of individual nano-material under stress state. The characterization of the invention is further provided two electrodes which is mounted to the sample but electrically insulated from the support bimetallic strips. The electrode has a good contact with the sample. The electrical conductivity between fixed two points on the sample can be measured during TEM image under stress.

In according with the illustrative embodiments, demonstrating features and advantages of the present invention, there is provided a sample grid for an in situ TEM which comprises two thermal bimetallic strips. The fabricated nano-material can be adhesive on the bimetallic strips. The bimetallic strips is movable when increase the temperature with heating TEM holder. The fixed nano-material can be elongated or compressed with the moving of thermal bimetallic strips. The structure-mechanical property relationships can be investigated by in situ TEM. The dynamic structure evolution process of the nano-materials can be real-time recorded by in situ high resolution TEM at atomic sale. At the same time, coating electrode on the surface of the bimetallic strips, we can in situ measure the electric property of individual nano-material under stress. The invention also provides the coupled measurements of applied force, electric and dynamic structure evolution.

Other objects, features and advantages of the invention will appear in the following detailed description thereof taken in conjunction with the drawings.

BRIEF DESCRIPTION OF THE DRAWINGS

The features and advantage of the present invention will be apparent from the following detailed descriptions of the preferred aspects of the invention in conjunction with the accompanying drawings wherein.

DETAILED DESCRIPTION OF THE INVENTION

Figure 1:
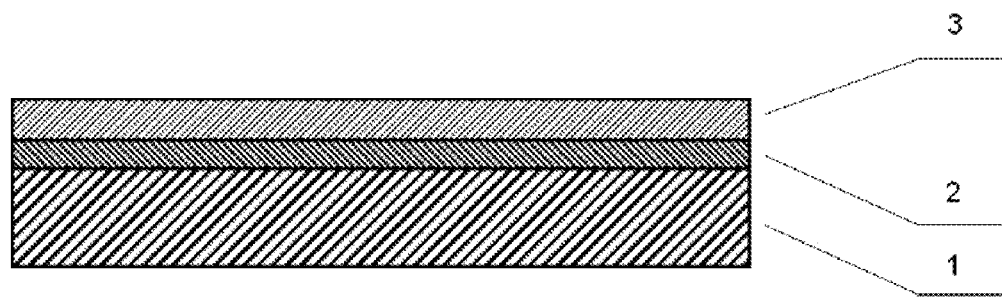
FIG. 1 illustrates the substrate after coating photoresist layer and sacrificial layer. The photoresist layer is on the top and the sacrificial layer stay in the middle.
Figure 2:
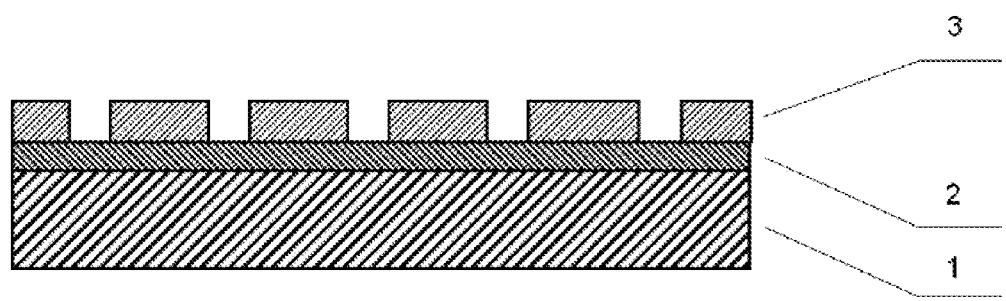
FIG. 2 shows a cross-sectional view of the patterns that are formed by exposure with the masks.
Figure 3:
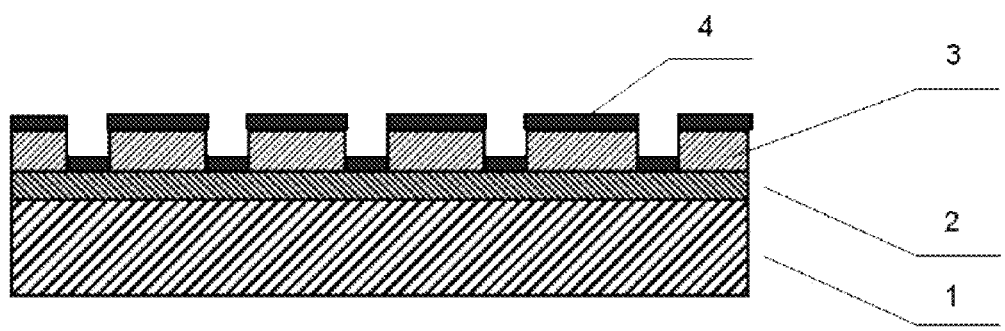
FIG. 3 illustrates a cross-sectional view of the nano-structure are coated on the patterns.

The making and using of various embodiments of the present invention are discussed in detail below with accompanying drawings. It should be appreciated that the present invention provides many applicable inventive concepts that may be embodied in a wide various specific contexts.

FIGS. 1-5 shows the state in which the nano-materials (4) such as nanowires and nanofilm are fabricated on Si substrate (1) by photolithography process.

Firstly, a sacrificial layer (2) was deposited onto the Si substrate (1). And then, spin coating a photoresist layer (3) above the sacrificial layer (2). Thirdly, different lines patterns or films were generated using photolithography after exposure. Lastly, the nano-materials (4) was deposited on the patterns, and then both of the photoresist and the material deposited on the photoresist are removed by ultrasonic cleaning the substrate, the various patterns of nanowires or thin nano-films are obtained.

FIGS. 6a and b illustrates a schematic view of the process of the fabricated nano-structure adhesion to two bimetallic strips (7).

The bimetallic strips (7) were fixed on an insulated metal ring (6), which can be implemented by coating an insulated layer on the metal with good thermal conductivity. Usually the insulated metal ring was in the diameter of 3 mm, and the ring and bimetallic strips electrically insulated from each other. The gap between two bimetallic strips is adjustable from 0.002 mm to 1 mm in according with the size of nano-material.

The nano-material on the Si substrate was fixed on the bimetallic strips by thin glue (5) and keeping the direction of longer side of the nano-materail was perpendicular to the gap of the two bimetallic strips. And then, the sacrificial layer (2) was removed by chemical corrosion and the nano-material specimen (4) was released from the Si substrate (1). The specimen was obtained with which two terminals were mounted on bimetallic strips of (6) and (7).

Figure 7:
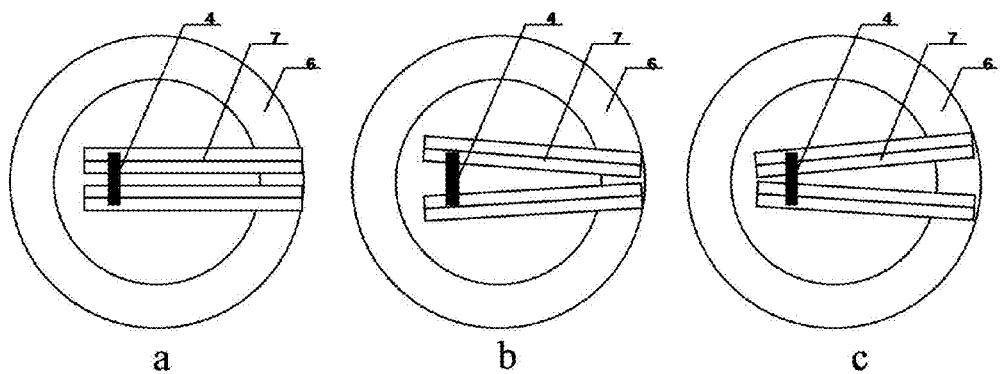
FIG. 7 illustrates a plan view of the fabricated nano-structure fixed on two bimetallic strips of TEM sample grid with parallel(a) or V-shaped(b,c).

FIG. 7 illustrates a plan view of the fabricated nano-structure fixed on two bimetallic strips of TEM sample grid.

Further, one of the bimetallic strips (7) can be replaced by the cantilever with stiffness coefficient k. The three dimension size of cantilevers were as follow: the thickness of between t=0.05-0.3 mm, width of between w=0.25-1 mm, length of between l=1.5-2.5 mm. The stiffness coefficient k of the cantilever was defined by the three-dimensional size and young's modulus of cantilever. The calculate formula of the stiffness coefficient k is: $k=Ywt3/4l3$. (Thereinto, Y represent the young's modulus of used material of cantilever; t, w, l, represent the thickness, width, and length of the cantilever). The interactive force f applied on specimen can be calculated by measuring the perpendicular displacement x of the cantilever. Firstly, nano-materials were drived by bimetallic strip, and then the cantilever was stretched by nano-material. During tensile process, the cantilever was bended towards the direction of bimetallic strip movement, so the mentioned "perpendicular displacement x" is the maximum bending distance of cantilever along pulling direction. According to the stiffness coefficient k of the cantilever, we can calculate the interactive force $f=kx$. (Thereinto, k represents the stiffness coefficient, x represent maximum perpendicular displacement of cantilever). The stain of nano-material can be calculated by sequence image analyses. As a result the stress and strain can be calculated applying on the nano-material specimen (4).

Further, for the in situ electrical measuring, a conductive layer such as a metal thin layer as the conductive electrodes (8) was deposited above the bimetallic strips (7). The conductive layer is brought into contact with specimen at fixed locations. The conductive layer and electrical wires (9) are electrically connected together. The electrical wires (9) are connected with the TEM sample holder.

The grid with sample was mounted to TEM sample holder. And then the TEM sample holder was mounted in a transmission electron microscopy.

With the grid and heating TEM holder or electrical TEM holder according to the described above, mechanical and electrical characteristics of individual nano-material can be measured during TEM images or before and after TEM image which is recorded using films, CCD camera or other means.

Accordingly, embodiments of the present invention include methods of fabricating, transferring and mounting the nano-material specimen and the apparatus of in situ TEM grid with two bimetallic strips which can be applied to investigate the electro-mechanical-property relationships and recorded simultaneously by real-time TEM images.

Figure 6:
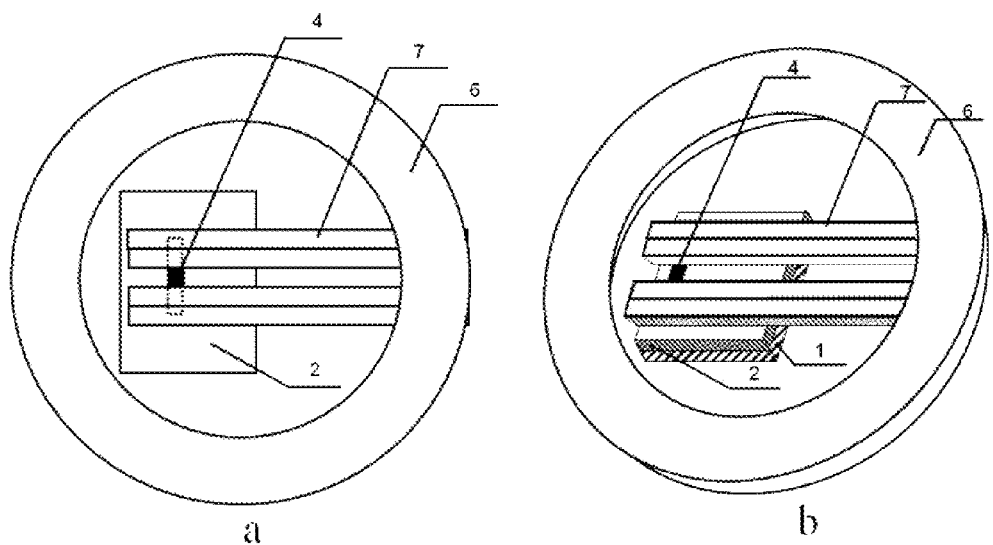
FIG. 6a and b illustrates a schematic view of the process of the fabricated nano-structure transfer to two bimetallic strips.

Further embodiments of the present invention can be implemented by adopting following steps:

1. Select a metal ring (such as copper) with good thermal conductivity in 3 mm diameter, coating a insulating layer on the surface. Each end of two bimetallic strips are mounted on the insulating ring with parallel or V-shaped (FIG. 6, 7). The size of bimetallic strips are of 0.05-0.3 mm thickness, 0.25-1 mm width and 1.5-2.5 mm length. The distance of two bimetallic strips can be adjusted between 0.002-1 mm according the length of nano-material.

Figure 4:
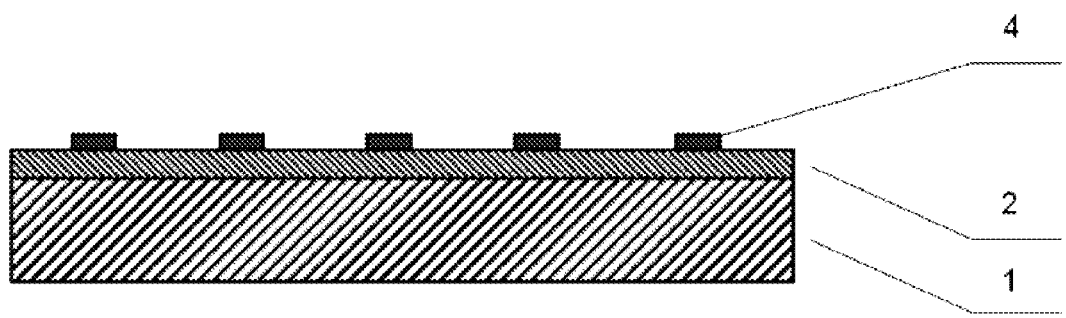
FIG. 4 illustrates a cross-sectional view of the fabricated nano-structure patterns after clearing the photoresist layer.
Figure 5:
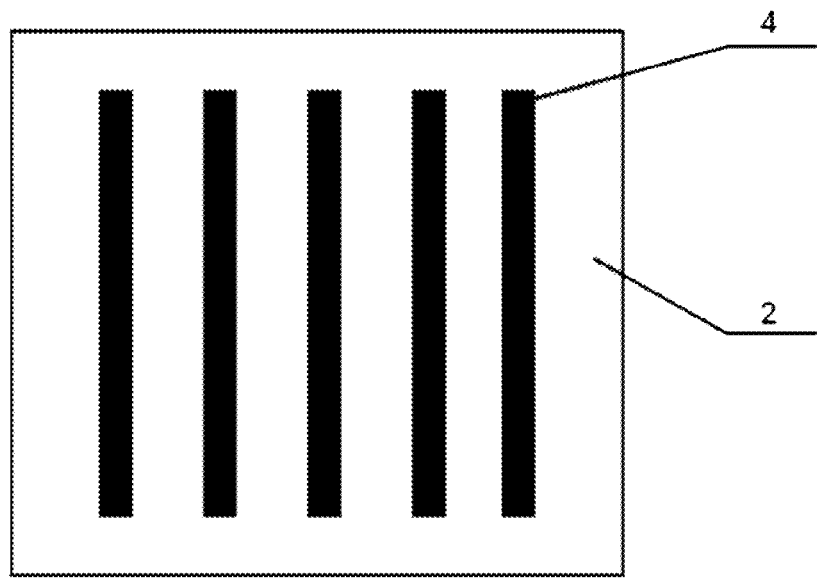
FIG. 5 shows a plan view of the fabricated nano-structure patterns on Si substrate.

2. Deposit a sacrificial layer (2) onto the substrate (1), spin-coating a photoresist layer (3) (FIG. 1), using photolithography to generate the lines patterns or films (FIG. 2), after deposition of nano-materials to form the nano-material patterns (FIG. 3), ultrasonic cleaning the substrate (1) in acetone, the nano-materials sample (4) were obtained (FIG. 4, 5).

3. Coating a thin glue layer (5) onto the upper side of the bimetallic strips (7) evenly. The glue layer has ability to fix nano-material quickly which can be AB glue, silver glue or 502 glue.

And then the sample (4) is glued on the bimetallic strips (7). With holding a period of time, the nano-materials (4) are cemented to bimetallic strips (7) fast. At this time, etch away sacrificial layer (2) with the corrosion solution for obtaining the device (FIG. 7), and then remove impurities by ultrasonic cleaning with deionized water. The corrosion solution can replace by HF, HNO3 NaOH, KOH, et al. It is important that the corrosion solution can remove the sacrifice layer but not corroded the nano-materials and bimetallic strips.

Figure 8:
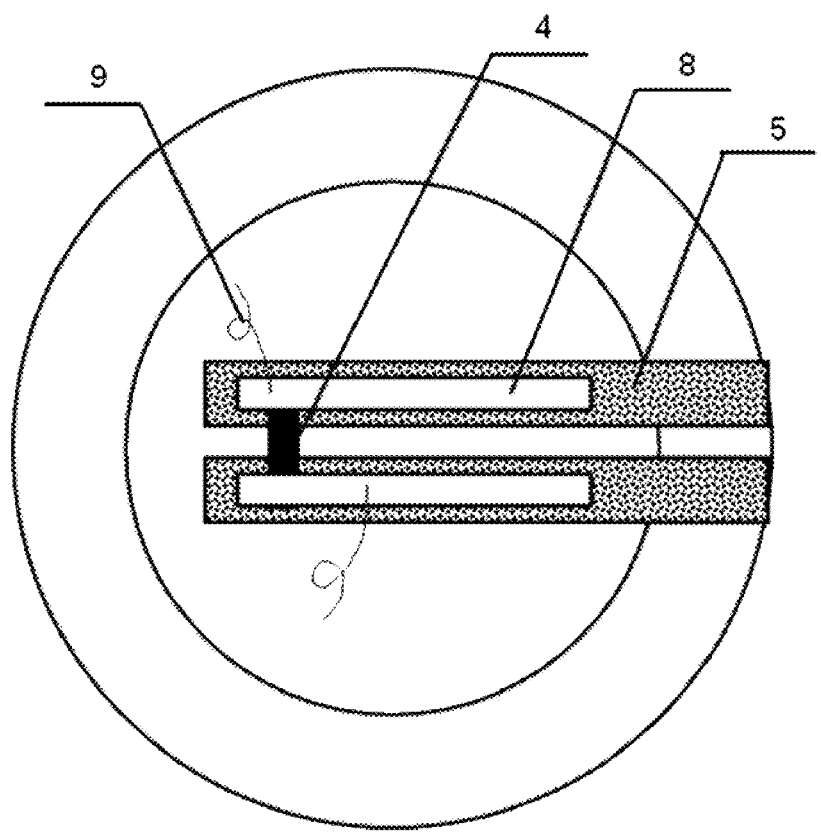
FIG. 8 illustrates a plan view of the fabricated nano-structure with thin film electrodes and metal wires on two bimetallic strips of TEM sample grid.

4. Spin-coating a photoresist layer, prograss following steps, as photolithography, exposure, developing, and then depositing a metal film layer of good electrical conductivity as electrodes (8) which stick tightly on the bimetallic strips. In this way, both ends of nano-materials (4) are nipped in the middle of bimetallic strips (7) and metal electrodes (8), removing photoresist by ultrasonic cleaning in the acetone. Leading wires (9) out of the metal electrodes (8) with the help of pressure welding machine (FIG. 8). Finally, the whole device is connected to the TEM samples holder, and then is placed into the TEM.

EXAMPLE

The device carrying nano-materials from top to bottom shows as follows: insulated ring with thickness of 0.15 mm; bi metallic strips, which are combined of the alloy $Mn_{72}Ni_{10}Cu_{18}$ with the bigger thermal expansion coefficient and the alloy $Ni_{36}$ with the smaller thermal expansion coefficient. Making the part of two bimetallic strips with the bigger thermal expansion coefficient be close the gap of two bimetallic strips, and make the bimetallic strips of smaller coefficient of thermal expansion in the external. The thicknesses of bimetallic strips are less than 0.1 mm and the width of 0.25 mm, the length of 2 mm. The pairs of bimetallic strips placed on the insulating ring are parallel, one end of bimetallic strips are fixed on the top of insulating ring, the other end of the bimetallic strips are hanged inside of the insulating ring. The top of two bimetallic strips lie in the same horizontal surface, the distance of two bimetallic strips was about 0.05 mm. Plating a silica layer of thickness about 200 nm onto the silicon wafer is by the way of Plasma Enhanced Chemical Vapor Deposition. Spin-coating a photoresist layer of thickness about 2 μm onto the silica layer, using lithography mask to exposure, and then imaging to obtain the required patterns. A copper layer of thickness 100 nm is deposited to get the pattern of nano-materails. After that, putting the wafer into the acetone is needed, the processes of ultrasonic cleaning will take about 5-10 minutes until the photoresist attached on the substrate is cleaned away. The nano-copper lines are left on the silica wafer, the copper lines in the 250 μm long, with width of 2 μm, with thickness of 0.1 μm.

Let the upper side of bimetallic strips face down, make the gap of two bimetallic strips are vertical to the longer side of nano-materials, and then attached to the silicon wafer which carry the nano-materails. The bimetallic strips cement with silicon wafer by holding to dry the combined device. Etching away silica layer in the dilute HF solution of concentration 0.5% less than 1 minute, bimetallic-strips together with nano-materials samples are released from the silicon wafer. After that, the combined device is cleaned with deionized water several times and 2 minutes each time, so the impurities of the bimetallic strips are removed. Spin-coating the photoresist layer of thickness 500 nm, and then using lithography mask to exposure, imaging etc. a good conductive gold layer was deposited as the metal film electrodes by mean of electron beam evaporation. By the help of light microscope, the vapor deposition metal film electrodes lying on the bimetallic strips can be observed, and both ends of the nano-copper films are nipped between the bimetallic strips and metal film electrodes. Lead the aluminum wires out of the metal film electrodes by ultrasonic welding, and then weld the other ends of the aluminum wires to the TEM samples holder, which has the function of heating and electrification.

Firstly, the attractive regions on the nano-copper films are found by observing in TEM and then heating and electrify to the TEM samples holder. With the temperature increasing from 20° C. to 200 ° C. in heating stage, bimetallic strips initiate to produce bending deformation, result in that the nano-copper films fixed on the bimetallic strips stretching slowly. During deformation processes, the high-resolution images can be recorded in situ through the CCD imaging systems. At the same time, the electrical signals of the samples are tested in situ under electrification, the changes of electricity can be captured by Semiconductor Parameter Analyzing Instruments. Thus, the relevance of electrical properties and micro-structure of the nano-copper films can be also revealed under stress state.

Figure 9:
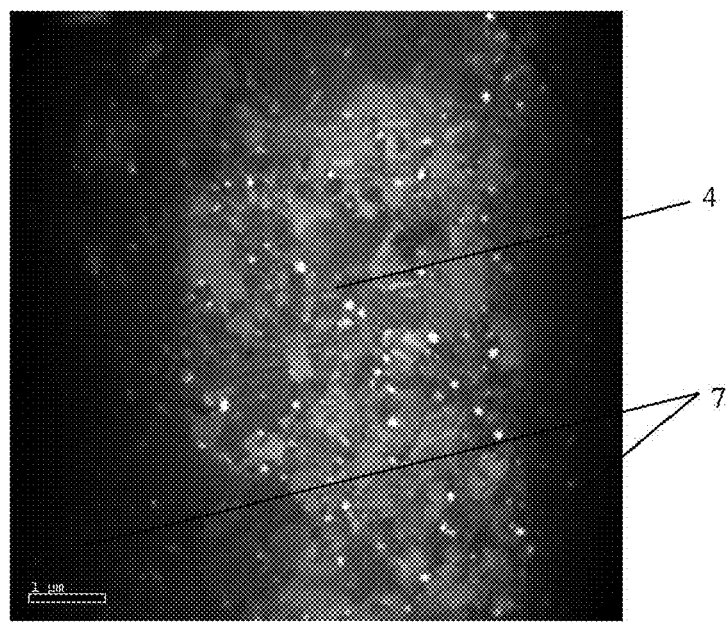
FIG. 9 illustrates the in situ TEM image of copper thin film fixing on two bimetallic strips at 40 degree.
Figure 10:
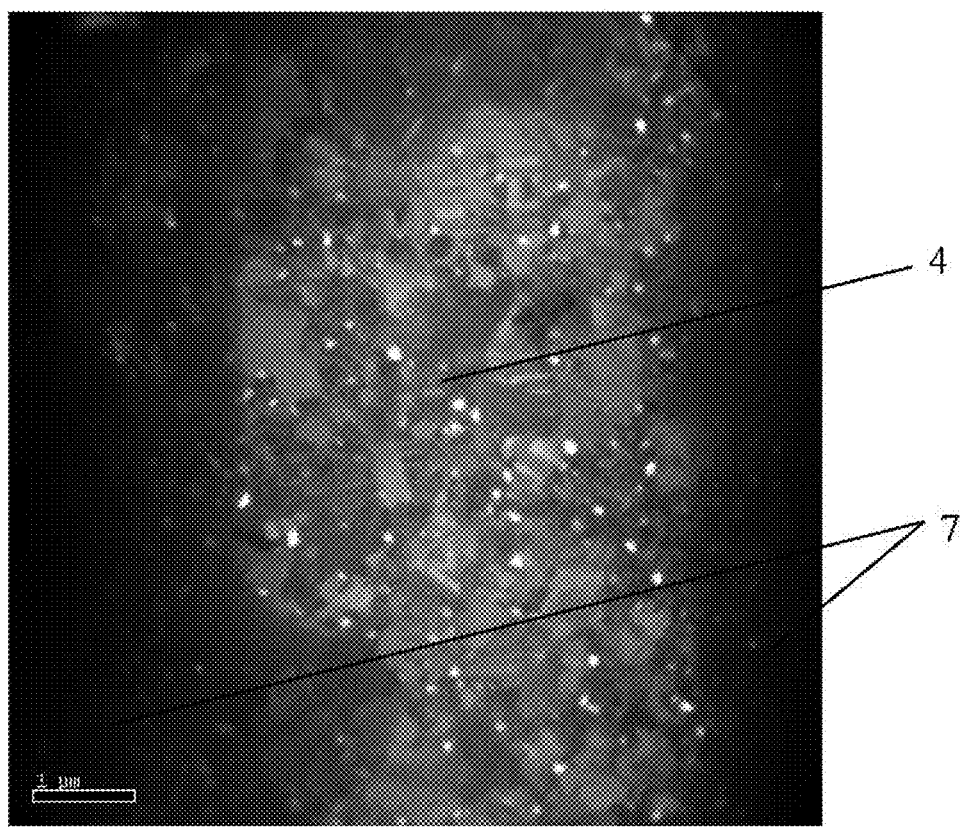
FIG. 10 illustrates the in situ TEM image of copper thin film at 50 degree, showing the distance of two bimetallic strips wider than the FIG. 9, indicating the film under strian.

FIG. 9 and FIG. 10 were the TEM images, right and left sides of the images with black contrast are the bimetallic strips, the nano-copper films were fixed under two metal film electrodes. The grains in the nano-copper films contained many of growth twins, and the grains varied their contrast with different crystallography orientations. The bimetallic strips moved towards right and left sides as a result of the bimetallic strips deformation, so the distance of bimetallic strips increased about 15 nanometers. In other words, the nano-copper films were elongated about 15 nanometers. During nano-copper films deformation process, the change of twins and stacking faults of the nano-copper films are observed and recorded. Meanwhile, the ten voltages were loaded to two metal film electrodes to measure the current change of the nano-copper films.

What is claimed is:

1. A device for measuring electromechanical properties and microstructure of nano-materials under stress state, comprising:

two bimetallic strips placed on an insulated metal ring plated with insulating paint, wherein the two bimetallic strips are placed in parallel or V-shaped to insulated metal ring on the same plane, one end of each bimetallic strip is fixed on the insulated metal ring, the other end of the bimetallic strip hangs inside of the insulated ring, the distance of two bimetallic strips were controlled within 0.002-1 mm.

2. The device according to claim 1, wherein one of the bimetallic strips is replaced by a leaf spring.

3. A method for measuring electromechanical properties and microstructure of nano-materials under stress state, comprising the following steps:

1), depositing a sacrificial layer on a substrate, forming a photoresist layer over the sacrificial layer, patterning the photoresist layer, depositing a nano-material over the patterned photoresist layer and the sacrificial layer, and ultrasonic cleaning the substrate to remove the photoresist layer so as to obtain a nano-material film with a line pattern deposited on the sacrificial layer;

2), providing two bimetallic strips placed on an insulated ring, coating a layer of glue on one side of the bimetallic strips, attaching the glue-coated side of the bimetallic strips to the line-patterned nano-material film, holding to cement the line-patterned nano-material film with the bimetallic strips, etching to remove sacrificial layer so that the bimetallic-strips together with the line-patterned nano-material film are released from the substrate;

3), forming an electrode on each of the bimetallic strips, so that portions of the line-patterned nano-material file are sandwiched between the bimetallic strips and the corresponding electrode, leading wires out from the electrodes;

4), finding the region of interest in the line-patterned nano-material film by observation in TEM, and then heating and electrifying a TEM sample holder, wherein, with the temperature increasing in heating stage and electrifying, the bimetallic strips bend due to different coefficient of thermal expansion, the line-patterned nano-material film fixed on the bimetallic strips undergoes uniaxial tensile or compressive deformation.

\* \* \* \* \*